United States Patent [19]

Rizzo, III

[11] Patent Number: 5,800,530

[45] Date of Patent: Sep. 1, 1998

[54] INTRA-OCULAR LENS SYSTEM INCLUDING MICROELECTRIC COMPONENTS

[76] Inventor: Joseph Rizzo, III, 220 Commonwealth Ave., Boston, Mass. 02116

[21] Appl. No.: 516,711

[22] Filed: Aug. 18, 1995

[51] Int. Cl.$^6$ ............................................. A61F 2/16
[52] U.S. Cl. ................................................... 623/6
[58] Field of Search ............................ 623/6; 351/160 R, 351/161

[56] References Cited

U.S. PATENT DOCUMENTS

| | | |
|---|---|---|
| 4,601,545 | 7/1986 | Kern . |
| 4,704,123 | 11/1987 | Smith ................................. 623/6 |
| 4,759,762 | 7/1988 | Grendahl . |
| 4,816,031 | 3/1989 | Pfoff ................................... 623/6 |
| 5,108,429 | 4/1992 | Wiley . |
| 5,171,266 | 12/1992 | Wiley ................................. 623/6 |

*Primary Examiner*—Mary Beth Jones
*Attorney, Agent, or Firm*—Choate, Hall & Stewart

[57] ABSTRACT

Dynamically functional intra-ocular prosthesis. The prosthesis includes an implantable intra-ocular lens and microelectronic components mounted on the lens. One embodiment is a variable focal length implantable intra-ocular lens system for adjusting the focal length of the implantable lens. In one embodiment, a micromotor changes the tension in a band encircling the peripheral portion of the deformable lens changing its shape to vary its focal length. Another embodiment is an artificial intra-ocular lens which serves as a holding substrate for microelectronic components that form part of a prosthesis to stimulate the neural elements of the eye to restore vision to patients who are blind from retinal disease.

7 Claims, 1 Drawing Sheet

INTRA-OCULAR LENS SYSTEM INCLUDING MICROELECTRIC COMPONENTS

BACKGROUND OF THE INVENTION

Implantable intra-ocular lenses are routinely used in surgeries in which a cataract is replaced with an artificial lens. These artificial intra-ocular lenses are usually made of plastic or an elastomer such as silicone and are designed to provide some fixed optical strength. Patients almost always require glasses after cataract extraction to improve both near and distant vision because these artificial lenses cannot self-adjust to varying strengths. Some newer intra-ocular lenses contain two optical powers thereby creating a bifocal lens. Regardless of the materials used or exact nature of the optical properties, these implantable intra-ocular lenses have been used heretofore only to provide static optical refraction (The only exception to this is the use of a coating that substantially reduces penetration of ultraviolet light through the lens). It has not been heretofore recognized that an implantable intra-ocular lens is an ideal platform for supporting microelectronic circuitry and components to make a dynamically functional eye prosthesis.

SUMMARY OF THE INVENTION

In one aspect, the invention is a dynamically functional eye prosthesis having an implantable intra-ocular lens and microelectronic components mounted on the lens. In one embodiment, the prosthesis is a variable focal length implantable intra-ocular lens system having a deformable intra-ocular lens. Electrical apparatus is provided for deforming the lens to change its focal length to a desired value. In one aspect, a band encircles a peripheral portion of the lens and the electrical apparatus alters tension in the band to alter the shape of the deformable lens to vary its focal length. Suitable electrical apparatus for altering the tension in the band includes micromotors and piezoelectric actuators. The band may also be made of a material such as a phase transition gel which acts as an "artificial muscle" which applies stresses to the periphery of the lens to alter its conformation thereby altering its focal length. In this way, the artificial lens with surrounding artificial muscle closely approximates the normal anatomy of the natural structures. In other embodiments, the lens supports photoelectric structure for receiving light passing through the lens to generate electrical energy. Distance measuring apparatus may also be mounted on the lens and arranged to control the deformation of the lens to adjust the focal length so that an object is in clear focus.

The microelectronic components that are incorporated into the structure of an intra-ocular lens according to the invention transform the heretofore static function of an artificial intra-ocular lens into a dynamically functioning prosthesis. An artificial intra-ocular lens is ideally suited to the task of supporting microelectronic components because the lens structural design provides a relatively stable platform once the lens is positioned in the ciliary sulcus that is located just behind the iris. In this location, microelectronic components are in a position to be exposed to light that is entering the eye and passing through the pupil. Further, the microelectronic components may protrude off the back surface of the intra-ocular lens into the relatively large posterior chamber of the eye. Supported in this way, the microelectronic components are not in contact with any of the ocular tissues except for the internal fluid that fills the back of the eye and thus will not alter the normal functioning of the eye. The internalized microelectronics supported on the lens permit the prosthesis to function independently of external supplies of power or signal to control their operation. In particular, photodiodes or other sources of electrical power are incorporated into the structure of the artificial intra-ocular lens to provide on-board, internally generated electrical power for operation of a prosthesis. Microelectronic components are provided to capture details of a visual scene and process them in a manner mimicking the normal function of the retina. In addition to altering lens focal length, this processed information may also be used to stimulate the nervous tissue of the eye to provide visual perception or some other physiological function such as the pupillary reaction to light.

The microelectronics endow an artificial intra-ocular lens with functions other than static optical power as known in the prior art. In one embodiment, the microelectronics create a variable focus intra-ocular lens that alters its diopteric power in accordance with the distance that some object of regard is located from the eye of the person. In this embodiment, the intra-ocular lens is made of an elastomer such as silicone or some other material whose shape is altered mechanically by externally applied forces. In one configuration, an encircling band placed around the circumference of the elastomeric lens alters the thickness of the lens according to the degree of external force that is applied. A thicker lens produces a stronger focusing lens element as would be needed to focus for the purpose of reading or attending to a relatively close stimulus.

The variable focal length artificial intra-ocular lens of the invention may also contain electronic components capable of measuring or estimating distance from the lens to a structure located in front of the lens. In one embodiment, the distance measuring apparatus sends a form of energy through the pupil and out of the front of the eye as could be achieved with acoustic waves or light. In this configuration the lens also contains an electronic element to sense the return of the signal to the eye and an estimation of distance is based on the temporal and other characteristics of the signal that reflects back into the eye. A microprocessor is included to process the information, which in turn is used to regulate the degree of change in shape of the lens. Alternatively, the distance estimating microelectronics can passively judge distance by attending to the high frequency components of visual scenes entering the eye and determining the diopteric power needed to properly focus the visual detail for the distance measuring device. The microprocessor then determines the degree to which the strength of the artificial intra-ocular lens would need to be altered to focus properly a visual image on the retina. This strategy of passively calculating distance and changing the shape of the intra-ocular lens may also be accomplished by having the microelectronic focusing element scan the image that is normally reflected from the retinal surface following illumination from incoming light.

The encircling band is tightened or loosened to effect a change in diopteric power by a micromotor or piezoelectric device that is powered and controlled by the other microelectronic components contained on the intra-ocular lens. The degree of activation of the micromotor, for example, is governed by the estimated need for diopteric strength mandated by the distance measuring apparatus.

DESCRIPTION OF THE PREFERRED EMBODIMENT

Figure 1:
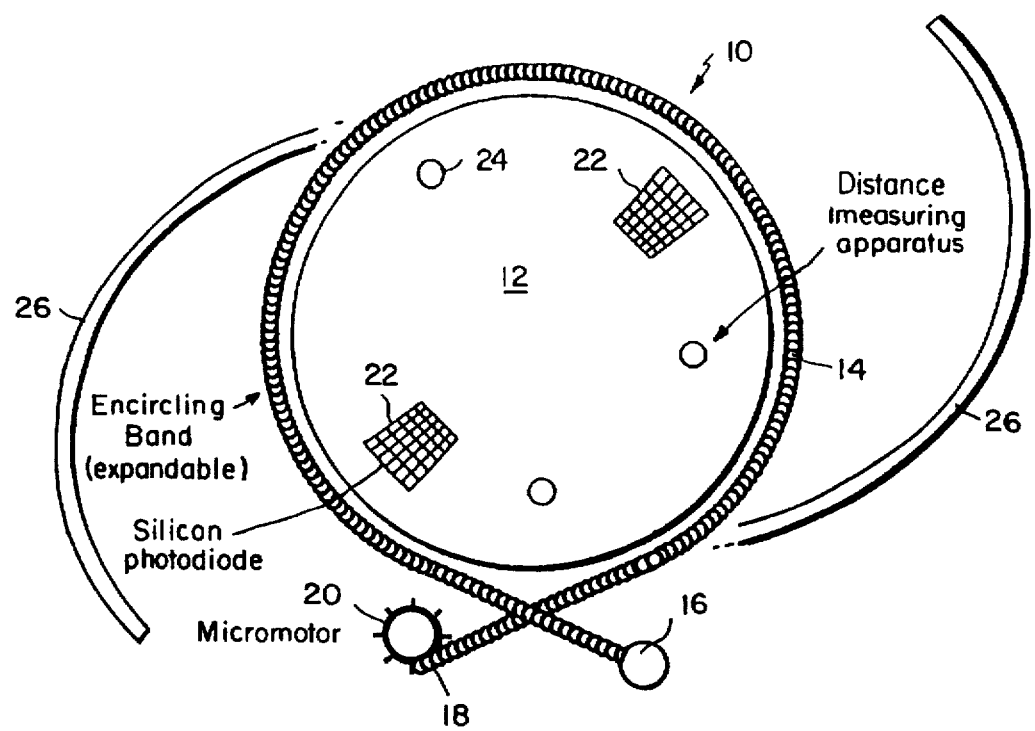
FIG. 1 is a schematic view of a variable focal length implantable intra-ocular lens.

With reference to FIG. 1, a variable focal length intra-ocular lens system 10 includes a deformable intra-ocular lens 12 made of a deformable material such as silicone. Surrounding a peripheral portion of the intra-ocular lens 12 is an encircling band 14. One end 16 of the band 14 is fixed in location and the other end 18 engages a micromotor 20. The micromotor 20 increases or decreases tension in the encircling band 14 to effect a change in the shape of the lens 12 thereby effecting a change in its diopteric power. It will be appreciated by those skilled in the art that the micromotor 20 may be replaced by, for example, a piezoelectric actuator. It will also be appreciated that the encircling band 14 may be replaced with a material that behaves as artificial muscle such as phase transition gels (in which case a micromotor or other actuator is not needed). These materials dramatically change their volume as a function of an applied voltage or ionic change in the surrounding environment. For example, a voltage is applied to an artificial muscle that reduces its volume thereby causing a tightening around the elastomeric lens to change its shape. An expansion of the volume of such an intra-ocular artificial muscle would produce the opposite effect thus reducing the optical strength of the elastomer that is the optical structure of the intra-ocular lens. The artificial muscle may be made of a polymer gel, such as polyacrylonitrile, that is made to be highly cross-linked. The derived polymer can be made to copolymerize with poly-acrylic acid. The volume of a copolymer such as this can be made sensititve to pH which can be changed by electrical stimulation or ion migration.

Power to drive the micromotor 20 or to cause a phase transition in an artificial muscle is provided by photodiode arrays 22. As will be appreciated by those skilled in the art, light passing through the lens 12 will interact with the photodiode arrays 22 to generate an electrical potential.

As shown in FIG. 1, distance measuring apparatus 24 may also be provided. The distance measuring apparatus 24 is powered by the photodiodes 22 and the distance measuring apparatus includes a microprocessor (not shown) for computing distance or an estimate of the distance. This computed information controls micromotor 20 to tighten or loosen the band 14 to change the focal length of the lens 12. As with conventional lenses, haptics 26 are provided for securing the lens within the eye during surgery.

The variable focus intra-ocular lens system 10 mimics a normal physiological ability of the lens of the eye to change its optical strength in accordance with the distance at which an object of regard is located from the viewer. This normal physiological process, known as accommodation, progressively wanes after age forty years or so. The great majority of patients who develop cataracts and then undergo surgical extraction of the cataractous lens are generally over sixty years of age and therefore no longer have the natural ability to adjust their focus. Any other deformable intra-ocular lens (without microelectronic components) would not be able to change its shape and therefore adjust its optical strength based upon natural accomodative control mechanisms that are no longer functional in these older patients. Therefore, these patients must wear glasses after undergoing surgery if they desire to have adequate focus at near and far distances. Further, the pre-operative choice of a particular strength of intra-ocular lens to implant may not prove to be accurate once the lens in positioned inside of the eye and thus this also commits the patient to the use of glasses. The variable focus intra-ocular lens of the invention may eliminate the need to use spectacles following cataract extraction.

Figure 2:
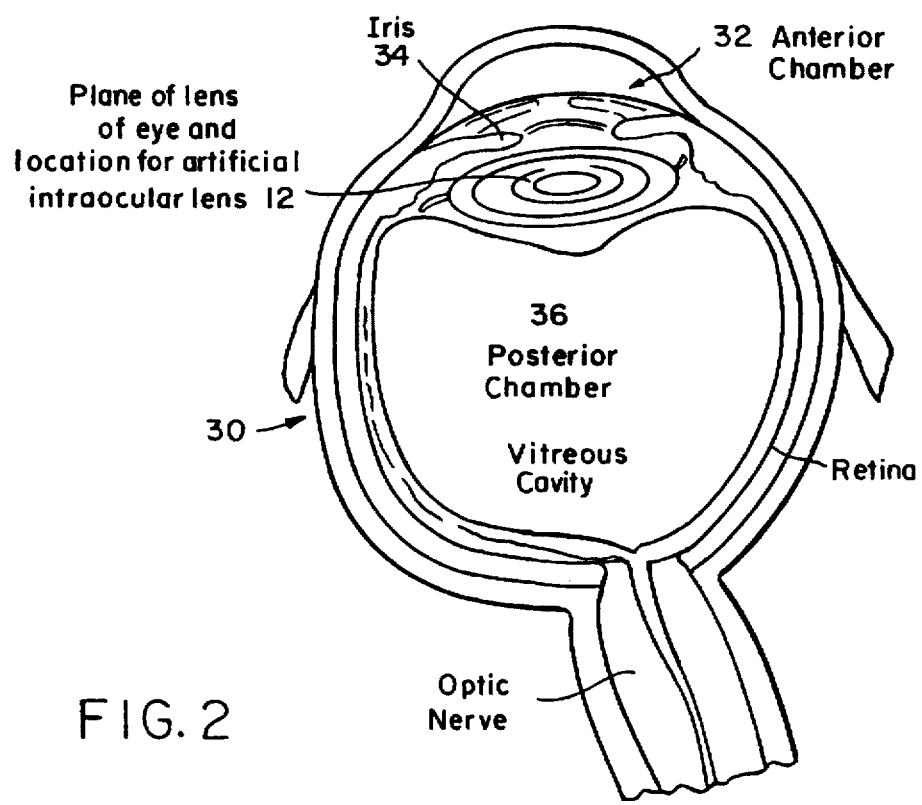
FIG. 2 is a schematic illustration of the human eye including an implanted artificial intra-ocular lens.

The variable focus intra-ocular lens system 10 is implanted into an eye as will be described in conjunction with FIG. 2. A human eye 30 includes an anterior chamber 32, iris 34 and posterior chamber 36. The artificial intra-ocular lens 12 is implanted in the location as shown using conventionally known surgical techniques.

Microelectronic components mounted on an intra-ocular lens may also be used as part of a prosthetic to restore vision by stimulating neural elements of the eye to patients who are blind from retinal disease. In addition to internalized sources of electrical energy, like photodiode arrays 22, an artificial intra-ocular lens can carry microchips that respond to the natural light entering the eye or other sources of external input that are used to produce a pattern of electrical stimulation on the retina of the eye via a collection of electrodes positioned close to or on the surface of the retina. Prosthetic microelectronic components carried in the artificial intra-ocular lens can be physically connected to electrodes located on or slightly above the retina by wires or other conduits that transfer electrical power or signals. The forward positioning of the microelectronic components minimize the need for placement of these components on the retina as a base of support, which could cause injury to the retina that is the intended target of stimulation to restore vision to the blind. Alternatively, stimulation of the cellular or axonal elements of the retina is accomplished by projection of light or other form of energy from the artificial intra-ocular lens across the space of the posterior chamber of the eye. Production of visual perception by initiating neural impulses requires alteration in cellular membrane potential and this can be achieved by direct application of electrical current to the retina via electrodes, release of neuroactive chemicals or application of some other source of energy that directly or indirectly activates neural elements. For instance, light may be shone upon those photo-sensititve components positioned on the retina that themselves produce a localized electrical current in response to being illuminated. Many such photo-sensitive components may be positioned on the retina and be individually addressed by signal input by, for instance, making components that respond differentially to varying wavelengths of light.

The internalized microelectronic components of the invention may also provide perceptional awareness of external sources of radiation that are beyond the 400–700 nanometer range of response of the human eye. In this context, the internalized components are adapted to detect infrared, ultraviolet or radiation from other regions of the electromagnetic specturm and initiate the same or similar electrical or other stimulus to the retinal surface that would be produced in response to visible light entering the eye.

The microelectronic elements set forth in this disclosure are made of biocompatible materials and encapsulated if necessary to prevent salt ions or other compounds within the eye from damaging or otherwise limiting their function. It is preferred that the artificial intra-ocular lens be designed so that the microelectronics mounted thereon may be separated from the body of the lens. This capability allows the replacement of non-functioning electronics or to enhance their function.

What is claimed is:

1. Variable focal length implantable intra-ocular lens comprising:

a deformable intra-ocular lens;

a band encircling a peripheral portion of the lens; and electrical means supported on the lens for altering tension in the band to alter the shape of the deformable lens to vary its focal length.

2. The lens of claim 1 further including a micromotor for altering the tension in the band.

3. The lens of claim 1 further including a piezoelectric actuator to change the tension in the band.

4. The lens of claim 1 further including distance measuring apparatus to control the electrical means for altering the tension in the band.

5. The lens of claim 1 further including power generating elements mounted on the lens.

6. The lens of claim 1 wherein the band encircling a peripheral portion of the lens is a phase transition gel forming an artificial muscle.

7. Variable focal length implantable intra-ocular lens system comprising:

a deformable lens;

a band encircling a peripheral portion of the lens;

a micromotor mounted on the lens and adapted to alter tension in the band to deform the deformable lens;

photodiode structure mounted on the lens for receiving light passing through the lens to generate electrical energy for operating the micromotor; and distance measuring apparatus mounted on the lens and adapted to control the micromotor to deform the lens to vary the focal length of the lens.

* * * * *